United States Patent [19]

Sundström

[11] Patent Number: 5,114,578
[45] Date of Patent: May 19, 1992

[54] SETTLING APPARATUS

[75] Inventor: Gustaf F. Sundström, Djursholm, Sweden

[73] Assignee: Stiftelsen Centrum for Dentalteknik Och Biomaterial I Huddinge, Huddinge, Sweden

[21] Appl. No.: 654,041

[22] Filed: Feb. 12, 1991

[30] Foreign Application Priority Data

Feb. 14, 1990 [SE] Sweden .................. 9000524

[51] Int. Cl.$^5$ .................. B01D 21/02
[52] U.S. Cl. .................. 210/256; 210/261; 210/262; 210/521; 210/532.1; 433/92; 433/97
[58] Field of Search .................. 210/256, 257.1, 259, 210/261, 262, 521, 522, 532.1; 433/92, 97

[56] References Cited

U.S. PATENT DOCUMENTS

| | | | |
|---|---|---|---|
| 2,613,811 | 10/1952 | Archibald | 210/110 |
| 3,399,135 | 8/1968 | Conley, Jr. et al. | 210/521 |
| 3,613,889 | 10/1971 | Reed | 210/522 |
| 3,812,970 | 5/1974 | Yamazaki | 210/521 |
| 4,115,279 | 9/1978 | Toft | 210/521 |
| 4,132,651 | 1/1979 | deJong | 210/522 |
| 4,151,075 | 4/1979 | Othmer | 210/706 |
| 4,326,952 | 4/1982 | Blake | 210/521 |
| 4,559,141 | 12/1985 | Gyulavari | 210/521 |
| 4,580,978 | 4/1986 | Motola et al. | 433/92 |
| 4,783,255 | 11/1988 | Bogusch | 210/522 |

FOREIGN PATENT DOCUMENTS

| | | |
|---|---|---|
| 2344316 | 10/1977 | France. |
| 54-104078 | 8/1979 | Japan. |
| 55-67304 | 5/1980 | Japan. |
| 1477688 | 5/1989 | U.S.S.R.. |
| 654642 | 6/1951 | United Kingdom. |
| 1238489 | 7/1971 | United Kingdom. |

Primary Examiner—Stanley S. Silverman
Assistant Examiner—Christopher Upton
Attorney, Agent, or Firm—Griffin Branigan & Butler

[57] ABSTRACT

A settling apparatus for the separation of amalgam from waste water in a dental procedure includes an inclined passage through which the water is caused to flow from below and upwards while depositing amalgam. The inclined passage has an inclination of between 3° and 15°. It is filled with a large number of thin-walled, narrow tubes, which contact each other in a side-by-side manner. The water flows from below and upwards through the tubes and through the channels between the tubes while amalgam is settled and deposited on the interior, as well as on the exterior, surfaces of the tubes.

9 Claims, 3 Drawing Sheets

Fig. 5.
Fig. 6.
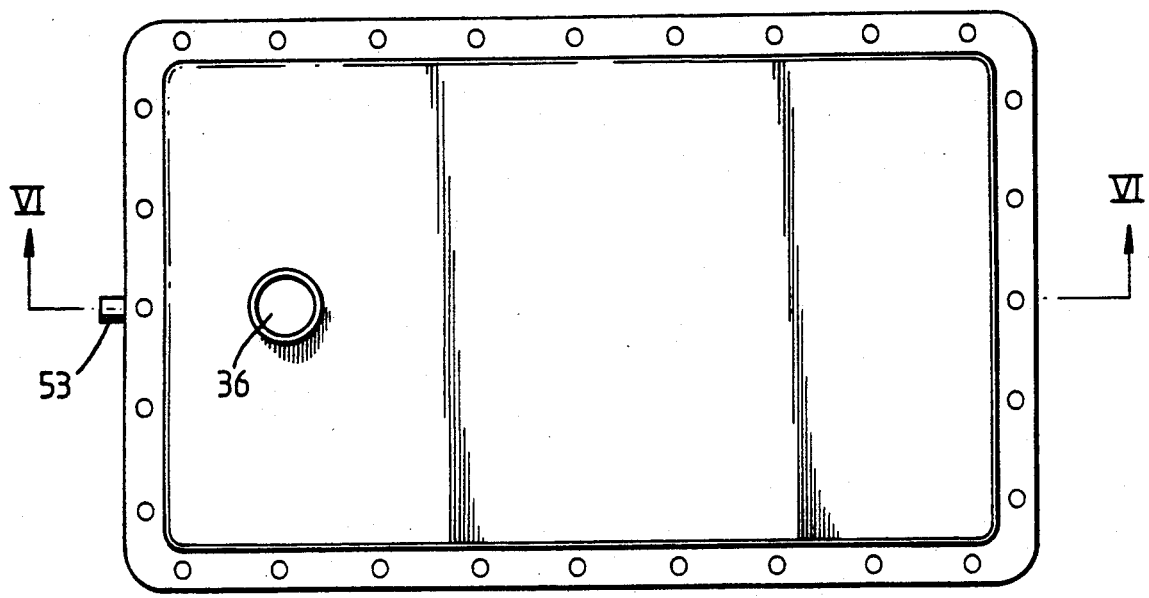
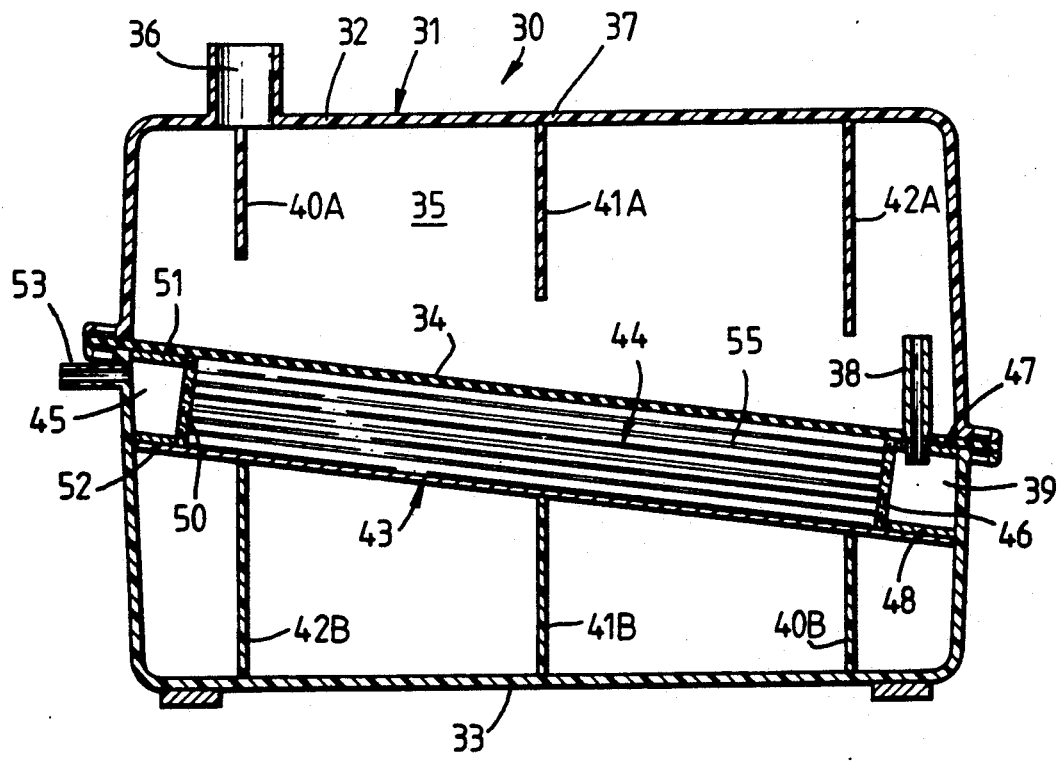

SETTLING APPARATUS

TECHNICAL FIELD

This invention relates to a settling apparatus, particularly an apparatus for the separation of amalgam from waste water from a dental procedure. An inclined passage is provided through which the waste water is caused to flow from below and upwards in the passage while depositing amalgam in the passage.

BACKGROUND OF THE INVENTION

Several different embodiments of settling apparatus comprising a plurality of parallel and inclined settling canals separated by lamellar elements are known to the art. By way of example may be mentioned those apparatuses which are described in the U.S. Pat. Nos. 2,868,384, 3,494,475, 3,741,892, and in the German patent No. 3 010 365. It is also known to utilize tubular settling channels, according to Swedish patent No. 352 243. Those apparatus which so far have been used in practice, however, have not satisfactorily met the specific demands which are required for settling apparatus intended for the separation of amalgam from waste water in dentists' practices, i.e. for applications where there is a comparatively small flow of water. The known apparatus either have been designed for very large installations and to comply with those specific demands which are raised in connection with such large installations, or they do not have satisfactory separation efficiency.

BRIEF DESCRIPTION OF THE INVENTION

The purpose of the invention is to provide a small, handy apparatus which can satisfy the specific demands which are required for apparatus for the separation of amalgam from the waste water from a dentist's practice or the like. Among these demands may be mentioned that the apparatus must have small dimensions, be inexpensive and simple to use, and have a very high separation efficiency as far as amalgam is concerned.

It is also a purpose of the invention that the apparatus, when it has been filled with removed amalgam to a certain degree, shall be readily reconditioned for further use.

These and other objects may be achieved when the above mentioned inclined space or passage is inclined with an inclination angle of between 3° and 15° from the horizontal, that it is filled with a very large number of thin-walled, narrow tubes which contact each other in a side-by-side manner, and that the water is caused to flow from below the tubes and upwards and through the tubes as well as through the channels formed between adjacent tubes, while amalgam is caused to settle and be deposited by direct contact on the interior, as well as on the exterior, surfaces of the tubes. Preferably the passage and hence the tubes have an inclination of 5°-10°.

The inclined passage suitably has a cross sectional area of between 2 000 and 20 000 mm². The tubes preferably have a circular cross section with an inner diameter of between 1 and 4 mm and a wall thickness of not more than 0.5 mm. Preferably they consist of thin-walled plastic tubes having a length of 100-400 mm. The inclined passage may have a circular, rectangular, or any other desired cross section.

According to a preferred embodiment the settling apparatus comprises a pre-settling chamber, which has a larger volume than the inclined passage which contains the tubes, and the inclined passage, according to a preferred embodiment, is part of a separate unit or cassette which can be removed from and replaced in the main part of the apparatus. By exchange of cassettes the apparatus can be reconditioned quickly when the tubes and the passage between the tubes have been loaded with amalgam to a predetermined degree. The exchange of cassettes may, for example, be made regularly and rather frequently according to a certain time schedule, while the cleaning of the larger pre-settling chamber may be performed less frequently. The cassette may consist of a cylindrical barrel in the form of a thicker outer tube, which, at least in that end thereof which is lowermost when the cassette is mounted in or on the settling apparatus, is provided with a bottom plate against which the narrow tubes may rest inside the thicker outer tube. In fluid communication with this bottom plate there may be provided a pre-chamber which communicates with the pre-settling chamber.

Further, according to another embodiment of the invention, the exterior of the apparatus may consist of a housing having upper and lower compartments, with the upper end lower compartments being separated from each other by an inclined partition wall. The inclination of the inclined partition wall is equal to the inclination of the inclined passage, which is provided in the lower compartment beneath the inclined partition wall, together with an inlet chamber for the inclined passage. The upper compartment defines a pre-settling chamber and a conduit is provided through the inclined partition wall in the lower part thereof between the pre-settling chamber in the upper compartment and the inlet chamber in the lower compartment. According to this embodiment, the tubes in the inclined passage rest directly or indirectly on support members provided in the lower compartment.

Further features and aspects of the invention will be apparent from the appending claims and from the following description of a preferred embodiments.

BRIEF DESCRIPTION OF DRAWINGS

In the following description of preferred embodiments reference will be made to the accompanying drawings, in which

FIG. 5 is a top view of a settling apparatus according to a second preferred embodiment; and FIG. 6 shows a vertical section through the settling apparatus along the lines VI—VI in FIG. 5.

DESCRIPTION OF PREFERRED EMBODIMENTS

Figure 1:
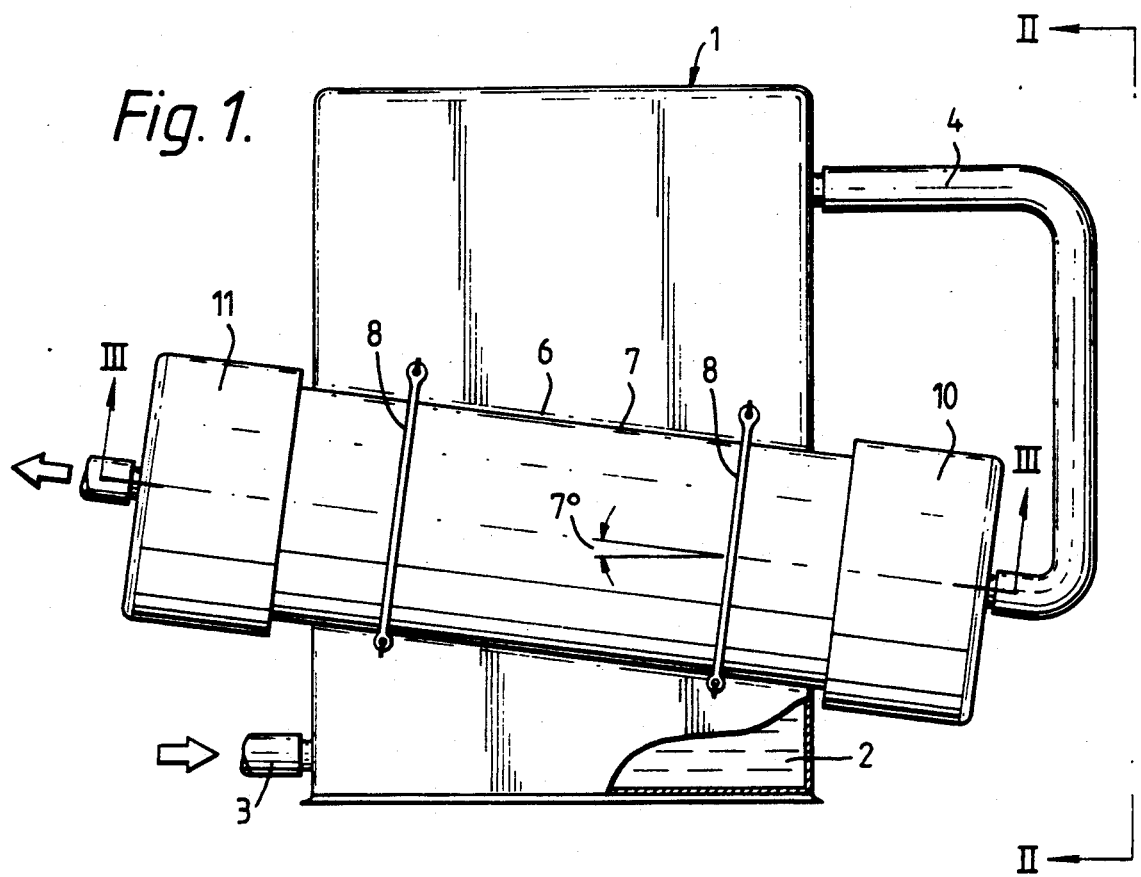
FIG. 1 is a side view of a settling apparatus according to a first preferred embodiment.
Figure 2:
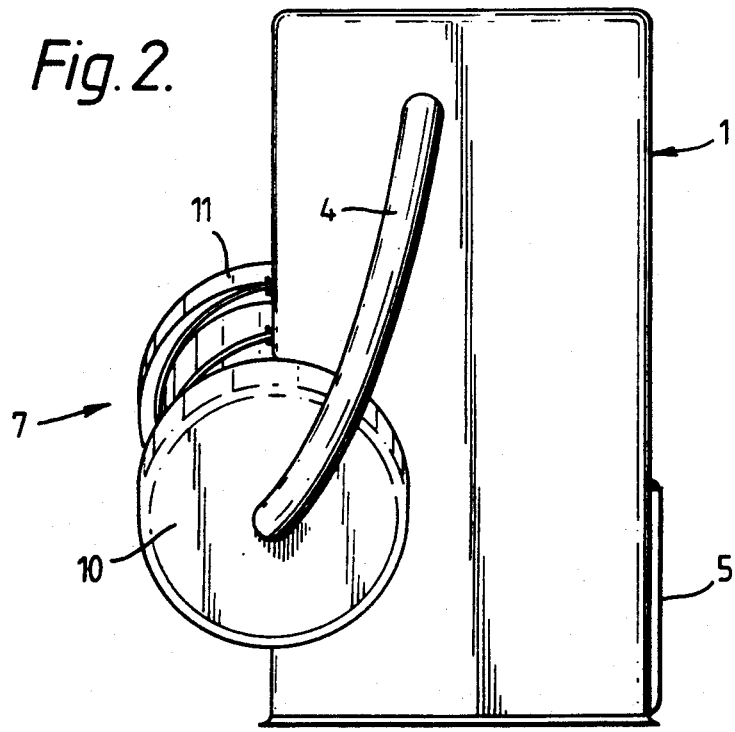
FIG. 2 is an end view of FIG. 1.

With reference to FIG. 1 and FIG. 2 the main part of the settling apparatus according to the first embodiment is designated 1. In this main part there is a pre-settling chamber 2 having an inlet conduit 3 and an outlet conduit 4 for waste water. Further there is provided a clean-out lid 5 on one side of the pre-settling chamber.

On the other side of the main part 1 there is provided an inclined recess 6, in which there is provided a removable cassette 7, which is secured in the recess 6 by means of a pair of rubber bands 8. The inclination of the recess 6 defines the inclination of the cassette 7, which is, in a most preferred embodiment, about 7° to the horizontal plane.

Figure 3:
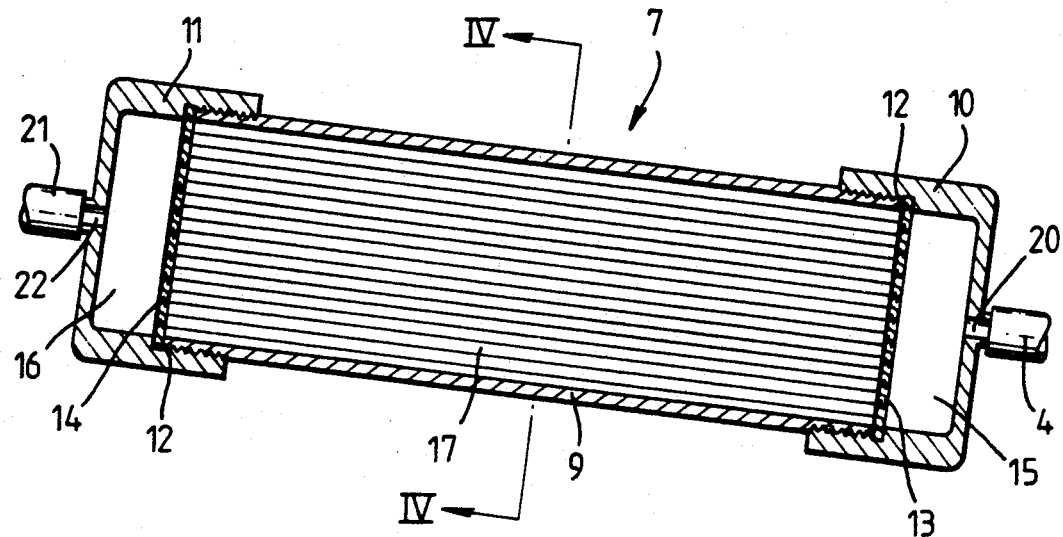
FIG. 3 shows a cross-sectional view of a settling cassette forming part of the settling apparatus, along the line III—III in FIG. 1.

The cassette 7 consists of an outer cylindrical barrel 9, which according to the embodiment has a circular cross section, although a rectangular and other cross-sections may be used. In each end of the barrel 9 there is a cap, e.g. a screw cap 10 and 11, respectively. As shown in FIG. 3, fastened between circular abutment surface 12 on the inside of caps 10 and 11, respectively, and the outside of barrel 9 are perforated plates, e.g. circular wire screens 13 and 14, respectively. Between these screens 13, 14 and the end portions of the caps 10 and 11 there is provided a lower inlet pre-chamber 15, and an upper end chamber 16, respectively.

Figure 4:
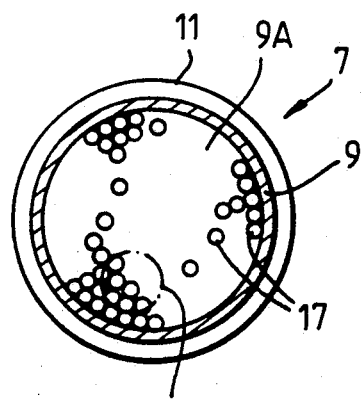
FIG. 4 shows a cross-sectional view of the settling cassette along the line IV—IV in FIG. 3.
Figure 4A:
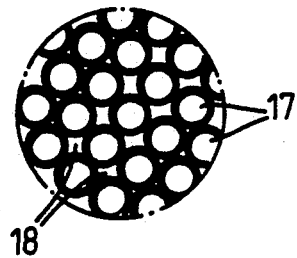
FIG. 4A shows enlarged details of FIG. 4.

The interior, inclined passage 9A (see FIGS. 4 and 4A) of the barrel 9 is filled with a plurality of small diameter, narrow, thin-walled plastic tubes 17, which are in a number that they contact each other in a side-by-side manner and in a more or less regular pattern and extend through the barrel 9, so that channels are formed between the tubes. The sizes of these channels may vary somewhat depending on irregularities in the arrangement of the tubes and also on the number of tubes, i.e. on how closely the tubes are packed. According to a preferred embodiment the tubes have a diameter of about 2.5 mm and a wall thickness of 0.5 millimeter or less, e.g. only a few tenths of a millimeter, i.e. a thickness which can be neglected with regard to the cross-section of passage 9A. The tubes 17 rest at their lowermost ends against the lower screen 13. Preferably the tubes 17 have the same length as the barrel 9 and are secured between the two screens 13 and 14. The previously mentioned outlet conduit 4 from the pre-settling chamber 2 is connected to an inlet opening 20 of the lower inlet pre-chamber 15, and a discharge conduit 21 for clarified water is connected to a discharge opening 22 in the end wall of the upper end-chamber 16.

When the settling apparatus is in use, waste water containing amalgam is flowed through the conduit 3 to the pre-settling chamber 2. Larger lumps of amalgam, tooth chips and other larger solid objects have been separated from this waste water by screening in a previous operation. The main part of remaining amalgam is deposited on the bottom of the pre-settling chamber 2. From the pre-settling chamber 2 the water is flowed to the cassette 7. In the inclined passage 9A in the cassette 7 the water is caused to flow slowly upwards from the pre-chamber 15 through the screen 13, and further through the large number of tubes 17 as well as through the spaces 18 between these tubes 17 and up to the upper end-chamber 16 and further out through the discharge conduit 21. Due to the facts that the tubes 17 are narrow and that water also passes between the tubes in the spaces 18, laminar flow of the water is achieved. The laminar flow in combination with the low flow speed of the water and the small inclination, preferably about 7°, of cassette will cause even extremely small amalgam particles to be deposited by settling or by direct contact on the exterior, as well as on the interior, surfaces of the walls of the tubes 17. The flow of the waste water through the apparatus may be caused by any convenient means, such as by gravity, by syphon action, by pumps or the like.

When the cassette 7 has been filled with amalgam to a certain degree or when the settling process has been conducted for a certain pre-determined period of time, the cassette 7 is removed and is replaced by a new cassette containing clean tubes 17. The used cassette is sent to a commericial plant for recovery of the amalgam. At certain intervals, also the pre-settling chamber 2 is cleaned with respect to the amalgam which has been collected in pre-settling chamber 2.

With reference now to FIG. 5 and FIG. 6 a settling apparatus of a second embodiment is general designated 30. All the parts of the apparatus are enclosed in a housing 31 consisting of two identical main parts, namely an upper half 32 of the housing, and a lower half 33. The two halves 32 and 33 consist of injection molded plastic material and may be made in the same molding tool or die which reduces the production cost. The two halves 32 and 33 are secured to each other along an inclined parting plane, for example, by clamping together the two halves along a circumferential edge portion of an inclined partition wall 34 in said inclined plane. The inclined partition wall 34 may consist of rubber or a polymeric material which may serve as a gasket between the two halves 32 and 33.

The inclined partition wall 34 has an inclination of between 3° and 15°, preferably between 5° and 10° or for example 7°, with respect to the horizontal. The compartment in the housing 31 above the inclined partition wall 34 constitutes a pre-settling chamber 35 and may correspond to 50% of the whole volume of the housing 31. The pre-settling chamber 35 has an inlet 36 in the top portion or roof 37 of the pre-settling chamber 35 in the region of the top portion which is nearer of the inclined partition wall 34. In the bottom part of the inclined partition wall 34 there is provided a communication conduit 38 extending through the partition wall, establishing fluid communication between the pre-settling chamber 35 and an inlet chamber 39 beneath the inclined partition wall 34. Further, vertical baffles 40A, 41A, 42A extend downwards from the roof 37 between the inlet conduit 36 and the communication conduit 38, the length of said baffles 40A, 41A, and 42A successively being longer in relation to the slope of the inclined partition wall 34, as shown in FIG. 6.

In the bottom compartment defined by the lower half 33, which is preferably of the same size and configuration as the upper half 32, there are also vertical partition walls 40B, 41B, and 42B corresponding to the baffles 40A-42A in the upper compartment. The partition walls 40B-42B serve as supports for an inclined plate 43 which is parallel with the inclined partition wall and rests on said supports 40B-42B.

Between the inclined partition wall 34 and the inclined plate 43 there is an inclined passage 44 which has the same inclination as the inclined partition wall 34 and the inclined plate 43. The inclined passage 44 extends between the longitudinal side walls of the housing 31. In the lower end of the inclined passage 44 there is provided the inlet chamber 39 and in the upper end there is correspondingly provided an outlet chamber 45. The inlet chamber 39 is defined by a screen 46 which is integrated with top and bottom distance members 47 and 48, which contact the end wall of the housing 31. The outlet chamber 45 is correspondingly defined by a screen 50 and upper and lower space members 51 and 52, respectively. In the region of the outlet chamber 45 there is provided a discharge opening 53.

The passage 44 is filled with tubes 55 of the same type as have been explained in connection with the above described first embodiment. Like the tubes in the said first embodiment, the tubes 55 contact each other in a side-by-side manner so that, preferably, the whole volume of the passage 44 is filled with the tubes 55, and also so that channels are formed between the contacting tubes in a more or less regular pattern.

When the settling apparatus 30 is in use, water containing amalgam is fed through inlet 36 to the pre-settling chamber 35 where the main part of amalgam existing in the waste water is deposited on the inclined partition wall 34, wherein the baffles 40A, 41A, and 42A contribute to a flow pattern of water in the pre-settling chamber 35 which is advantageous to the settling procedure. From the pre-settling chamber 35 the waste water is fed via conduit 38 through the bottom part of the inclined partition wall 34 to the inlet chamber 39 beneath the lowermost part of the partition wall 34. From the inlet chamber 39 the waste water flows through the screen 46 and further through the large number of tubes 55 as well as through the channels between the tubes 55 and up to the outlet chamber 45 and out through the discharge conduit 53. In the inclined passage 44, which according to this embodiment has a rectangular cross section, the water will have laminar flow, as according to the previous embodiment, wherein even extremely small amalgam particles are deposited by settling or by direct contact on the exterior, as well as on the interior, surfaces of the walls of the tubes 55.

When the space 44 has been filled with amalgam to a certain degree or when the settling process has been conducted for a certain predetermined period of time, the apparatus is demounted; amalgam which has collected in the pre-settling chamber 35 is removed, and the tubes 55 are replaced by new ones, which may be in a cassette form, whereafter the apparatus is re-assembled.

I claim:

1. A settling apparatus for removing amalgam from waste water produced in a dental procedure, comprising a housing having upper and lower compartments separated from each other by an inclined partition wall, said upper compartment defining a pre-settling chamber; an inclined passage having an inclination to the horizontal of from about 3° to 15°; a plurality of tubes extending through said passage and the number thereof being sufficient that substantially all of the tubes contact other tubes in a side-by-side manner and form channels therebetween; means for flowing said waste water from said pre-settling chamber to a lowermost end of said passage and from said lowermost end of said passage through said passage, tubes and channels in laminar flow and out of said passage, wherein the inclination of said inclined partition wall is equal to the inclination of said inclined passage, said inclined passage being disposed in the lower compartment and beneath said inclined partition wall, and wherein amalgam in said waste water is settled in said pre-settling chamber and in and among said tubes and channels in said passage during said flowing of the waste water.

2. Apparatus according to claim 1, wherein the passage and the tubes are inclined at an inclination of 5°-10°.

3. Apparatus according to claim 1, wherein the inclined passage has a cross section area of between 2000 and 20000 mm$^2$, the tubes have a circular cross section, an internal diameter of between 1 and 4 mm, and a wall thickness of not more 0.5 mm.

4. Apparatus according to claim 1, wherein the passage and the tubes have a length of about 100-400 mm.

5. Apparatus according to claims 1, wherein the tubes rest at their lowermost ends against a perforated bottom plate, an inlet chamber is provided in fluid communication with the bottom plate, and the inlet chamber is in fluid communication with a pre-settling chamber.

6. Apparatus according to claim 1, wherein the circumferential edge portion of the inclined partition wall is clamped between an upper half of the housing defining said upper compartment and a lower half of the housing defining said lower compartment, and wherein the inclined partition wall also serves as a support for a gasket disposable between said upper and lower halves.

7. Apparatus according to claim 1, wherein the inclined passage is supported on members provided in said lower compartment.

8. Apparatus according to claim 1, wherein a conduit is provided through said partition wall in the lowermost part thereof between the pre-settling chamber in the upper compartment and an inlet chamber in the lower compartment, said inlet chamber being in fluid communication with said passage.

9. Apparatus according to claim 8, wherein vertical partition walls are provided in the upper and lower compartments, extending downwardly from a roof of the upper compartment and upwards from a bottom of the lower compartment, respectively, and an inlet conduit to said pre-settling chamber is provided in a part of the pre-settling chamber which is opposite to that of a part where said conduit between the pre-settling chamber and said inlet chamber is located, said partition walls in the upper compartment serving as baffle-members in the pre-settling chamber, and said partition walls in the lower compartment serving as support members for said inclined passage, the vertical length of said vertical partition walls in the pre-settling chamber increasing with the slope of the inclined partition wall from the inlet conduit to the said conduit from the pre-settling chamber to the inlet chamber, and the vertical length of said vertical partition walls in the lower compartment increasing along the length of the inclined pasage in relation with the inclination of the inclined partition wall.

* * * * *